United States Patent [19]

Bertrand et al.

[11] Patent Number: 4,849,417
[45] Date of Patent: Jul. 18, 1989

[54] ACETYLSALICYLIC ACID DERIVATIVE AND PHARMACEUTICAL COMPOSITION THEREOF

[75] Inventors: Claude Bertrand, Saint Germain les Corbeil; Gérard Wolff, Thiais, both of France

[73] Assignee: Rhone-Poulenc Sante, Courbevoie, France

[21] Appl. No.: 155,057

[22] Filed: Feb. 11, 1988

Related U.S. Application Data

[63] Continuation of Ser. No. 853,434, Apr. 18, 1986, Pat. No. 4,764,637.

[30] Foreign Application Priority Data

Apr. 19, 1985 [FR] France ................................ 85 05962

[51] Int. Cl.$^4$ ..................... A61K 31/615; C07C 69/14
[52] U.S. Cl. ...................... 514/162; 560/66; 560/143
[58] Field of Search ................... 560/66, 143; 514/162

[56] References Cited

U.S. PATENT DOCUMENTS

| | | | |
|---|---|---|---|
| 1,020,121 | 3/1912 | Berendes | 560/143 |
| 1,058,904 | 4/1913 | Richter | 560/143 |
| 1,113,742 | 10/1914 | Berendes | 560/143 |
| 3,382,273 | 5/1968 | Galat | 560/143 |

FOREIGN PATENT DOCUMENTS

| | | |
|---|---|---|
| 854944 | 8/1952 | Fed. Rep. of Germany . |
| 2492368 | 4/1982 | France . |

*Primary Examiner*—Werren B. Lone
*Assistant Examiner*—Vera C. Clarke
*Attorney, Agent, or Firm*—Stevens, Davis, Miller & Mosher

[57] ABSTRACT

The hydrated complex of magnesium acetylsalicylate and urea of formula

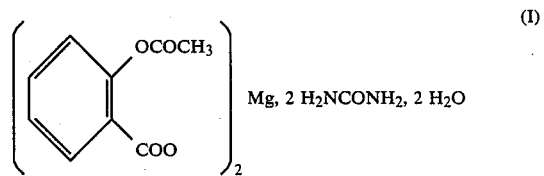

possesses exceptional analgesic and antipyretic properties. It may be crystallized from a solution obtained by reacting acetylsalicylic acid with magnesium carbonate in the presence of urea.

2 Claims, No Drawings

ACETYLSALICYLIC ACID DERIVATIVE AND PHARMACEUTICAL COMPOSITION THEREOF

This is a continuation of application Ser. No. 853,434 filed Apr. 18, 1986, now U.S. Pat. No. 4,764,637.

This invention relates to acetylsalicylic acid derivatives, their preparation, and pharmaceutical compositions containing them.

Acetylsalicylic acid (aspirin) is a drug which possesses exceptional analgesic and antipyretic properties but which, because of its acidity and low solubility, shows adverse effects on the body, especially when it is administered orally (poor gastric tolerance, bitter taste).

To avoid or reduce these disadvantages, it has been proposed to use aspirin in the form of a salt, to reduce its acidity and improve its solubility. Alkali metal (sodium) and alkaline earth metal (calcium, magnesium) salts have been proposed.

However, the processes described in the prior art for preparing aspirin salts frequently lead to products containing impurities which arise from the degradation of the acetylsalicylic acid during the salification, or to hydrated salts having inferior stability, which must be rapidly dehydrated. Moreover, the anhydrous salts are frequently hygroscopic and it is necessary to protect them effectively from moisture during their packaging and storage.

It has also been proposed to use more stable salts of aspirin such as organic salts or inorganic salts complexed with organic substances. More especially, it has been proposed to use complexes of calcium acetylsalicylate or magnesium acetylsalicylate with urea of formula:

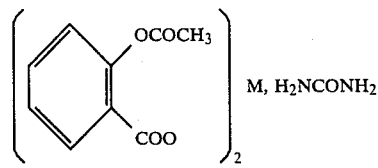

(II)

in which M denotes a calcium or magnesium atom.

The calcium acetylsalicylate/urea complex has been obtained by treating calcium acetylsalicylate with urea in an organic solvent.

The magnesium acetylsalicylate/urea complex has been obtained by concentrating a solution of magnesium acetylsalicylate and urea by evaporation under reduced pressure, followed by separation of the crystalline precipitate obtained.

However, although these complexes possess better stability than the corresponding metal salts, they must nevertheless be protected from moisture to preserve their initial properties.

It has now been found, and this forms the subject of the present invention, that the novel, hydrated magnesium acetylsalicylate/urea complex of formula:

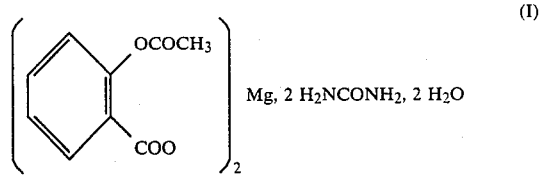

(I)

possesses a stability which is distinctly greater than that of the known salts or complexes.

More especially, although it is hydrated, the new complex of formula (I) is more stable than the hydrates of alkali metal or alkaline-earth metal salts of acetylsalicylic acid, and it is more stable than the anhydrous complexes which take up moisture on contact with atmospheric air.

The new complex of formula (I) is not hygroscopic. In consequence, it is not necessary to dehydrate it to be able to store it and convert it to pharmaceutically acceptable forms.

As a result of the good stability of the water of hydration, it is possible to dry the product by applying the usual techniques without adversely affecting the structure of the complex.

Moreover, since the presence of the water does not adversely affect the stability of the complex, it is possible to lyophilize solutions thereof, thereby making it possible to prepare new soluble forms for the administration of aspirin which could not be achieved with the hydrates of alkali metal or alkaline-earth metal salts.

According to a feature of the present invention, the new complex of formula (I) is obtained by forming a urea-containing supersaturated aqueous solution of magnesium acetylsalicylate by the reaction of acetylsalicylic acid with magnesium carbonate in aqueous medium containing urea, and crystallizing the said complex from said solution. Thus a concentrated solution of magnesium acetylsalicylate is produced in situ by the reaction of aspirin with magnesium carbonate in water in the presence of urea. The complex of formula (I) is then obtained by slow crystallization from the cooled supersaturated solution.

It is especially advantageous to work at a temperature of between 15° and 25° C., in order to obtain a sufficient rate of reaction between the acetylsalicylic acid and the magnesium carbonate, and to avoid deacetylation of the acetylsalicylic acid.

To obtain the complex of formula (I) an amount of urea at least equal to the stoichiometric amount corresponding to the formula (I) should be used. A 10 to 20% excess of urea is preferably used.

The concentration of the solution of the magnesium salt before the crystallization should correspond to an aspirin content of less than or equal to 300 g per kg of solution.

The crystallization of the complex of formula (I) from its solution should be performed at a temperature of between −2° and +2° C. In general, the crystallization, when performed at 0° C., is complete after 24 hours.

The crystallized complex of formula (I) is separated from the reaction mixture by filtration or decantation. Filtration is generally preferred, since it permits better washing of the product obtained with a suitable solvent such as acetone.

The complex of formula (I) thereby obtained can be dried under the usual conditions; preferably under reduced pressure, at a temperature of 20° C., without undergoing degradation.

The Example which follows illustrates the invention.

EXAMPLE

A homogeneous mixture of basic magnesium carbonate [$4MgCO_3.Mg(OH)_2.5H_2O$] (97.1 g) and aspirin (378 g) is prepared in a powder mixer. This mixture is introduced gradually in the course of 2 hours into a 2-liter reactor, equipped with a stirrer, containing urea (138.6 g) in water (700 cc) at a temperature of between 20° and 25° C. The solid dissolves and carbon dioxide is evolved. The initial pH of the urea solution is in the region of 7.5, and it stays in the region of 5.5–5.6 during the addition.

Stirring is continued for 30 minutes after the addition is complete. The solution is clarified by filtration. The clarified, transparent solution is cooled and maintained at a temperature of between $-2°$ and $+2°$ C. This solution is highly supersaturated with magnesium acetylsalicylate. Crystallization begins after one to two hours, and proceeds slowly. After 20 hours' stirring at a temperature in the region of 0° C., the crystals obtained are separated by filtration and then washed on a filter with acetone (700 cc) and finally dried under reduced pressure at a temperature in the region of 20° C.

The complex of formula (I) (223 g) is thereby obtained in the form of a white crystalline powder.

The analysis of the product obtained is as follows:

| Nitrogen | calculated 11.1% | found 11.1% |
|---|---|---|
| Magnesium | calculated 4.84% | found 4.89% |
| Aspirin | calculated 71.3% | found 71.4% |
| Water | calculated 6.7% | found 6.8% |

The salicylic acid content is between 0.36 and 0.47%.

The invention includes within its scope pharmaceutical compositions which contain the complex of formula (I) in combination with one or more diluents or adjuvants which are compatible and pharmaceutically acceptable.

As solid compositions for oral administration, tablets, pills, powders or granules can be used. In these compositions, the active product is mixed with one or more inert diluents such as starch, cellulose, sucrose, lactose or silica. These compositions can also contain substances other than diluents, for example one or more lubricants such as magnesium stearate or talc, a colouring, a coating or a lacquer.

The solid compositions for oral administration can take the form of lyocs.

As liquid compositions for oral administration, it is possible to use emulsions which are pharmaceutically acceptable, solutions, suspensions, syrups or elixirs, containing inert diluents such as water or liquid paraffins. These compositions can contain substances other than diluents, for example wetting, sweetening or flavouring products.

The compositions for parenteral administration can be sterile aqueous solutions or they can be suspensions or emulsions. As a vehile in these latter cases, polyethylene glycol, a propylene glycol, vegetable oils, especially olive oil, and injectable organic esters, e.g. ethyl oleate, can be used.

These compositions can also contain adjuvants, especially wetting agents, emulsifiers or dispersants.

Sterilization can be carried out in several ways, for example using a bacteriological filter, by incorporating sterilizing agents in the composition or by heating. They can also be prepared in the form of solid compositions made sterile, e.g. by irradiation, which can be dissolved in sterile water or dispersed in any other injectable sterile medium, possibly at the time of use.

The compositions for rectal administration are suppositories which can contain, in addition to the active product, excipients such as cocoa butter or a semi-synthetic glyceride.

The compositions according to the invention find especial use in human therapy as analgesics and antipyretics.

The dosage depends on the effect sought. It is generally between 200 and 200 mg per day for an adult, taken orally in one or more doses.

The Examples which follows illustrates a composition according to the invention.

EXAMPLE

Tablets having the following composition are prepared by the usual technique:

| complex of formula (I) | 250 mg |
|---|---|
| starch | 200 mg |
| colloidal silica | 40 mg |
| magnesium stearate | 10 mg |

We claim:

1. A hydrated complex of magnesium acetylsalicylate and urea of the formula:

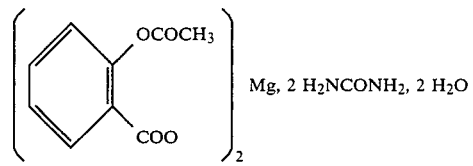

and analyzing as follows: nitrogen calculated 11.1%, found 11.1%; magnesium, calculated 4.84%, found 4.89%; aspirin, calculated 71.3%, found 71.4%; water, calculated 6.7%, found 6.8%.

2. An analgesic or antipyretic pharmaceutical composition comprising an effective analgesic or antipyretic amount of a hydrated complex of magnesium acetylsalicylate and urea of the formula

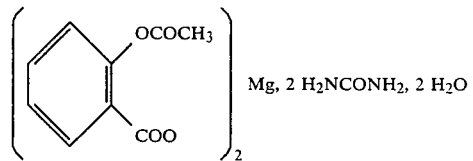

and analyzing as follows: nitrogen, calculated 11.1%, found 11.1%; magnesium, calculated 4.84%, found 4.89%; aspirin, calculated 71.3%, found 71.4%; water, calculated 6.7%, found 6.8%; in combination with one or more diluents or adjuvants which are compatable and pharmaceutically acceptable.

* * * * *